United States Patent [19]

Seidel et al.

[11] Patent Number: 4,858,602
[45] Date of Patent: Aug. 22, 1989

[54] BONE NAIL FOR THE TREATMENT OF UPPER ARM FRACTURES

[75] Inventors: Hartmut R. A. Seidel, Hamburg; Hans E. Harder, Probsteierhagen; Klaus F. A. Behrens, Rickling, all of Fed. Rep. of Germany

[73] Assignee: Howmedica GmbH Werk Schönkirchen, Schönkirchen, Fed. Rep. of Germany

[21] Appl. No.: 936,042

[22] Filed: Nov. 28, 1986

[30] Foreign Application Priority Data

Dec. 6, 1985 [DE] Fed. Rep. of Germany ....... 8534358

[51] Int. Cl.$^4$ ............................................. A61F 5/04
[52] U.S. Cl. ........................... 128/92 YY; 128/92 YZ
[58] Field of Search .......... 128/92 Y, 92 YY, 92 YZ, 128/92 YK, 92 YW, 92 YV, 92 YT, 92 YS

[56] References Cited

U.S. PATENT DOCUMENTS

| | | | |
|---|---|---|---|
| 2,490,364 | 2/1948 | Livingston | 128/92 YK |
| 2,699,774 | 5/1952 | Livingston | 128/92 YV |
| 4,091,806 | 5/1978 | Aginsky | 128/92 YY |
| 4,204,531 | 5/1980 | Aginsky | 128/92 YY |
| 4,227,518 | 10/1980 | Aginsky | 128/92 YY |
| 4,622,959 | 11/1986 | Marcus | 128/92 YZ |
| 4,632,101 | 12/1986 | Freeland | 128/92 YY |
| 4,697,585 | 10/1987 | Williams | 128/92 YK |

FOREIGN PATENT DOCUMENTS

| | | |
|---|---|---|
| 2359644 | 7/1975 | Fed. Rep. of Germany . |
| 2064915 | 6/1971 | France . |
| 895425 | 1/1982 | U.S.S.R. ......................... 128/92 YV |

Primary Examiner—John D. Yasko
Assistant Examiner—Mark F. Colosimo
Attorney, Agent, or Firm—Peter C. Richardson; Lawrence C. Akers; Elizabeth O. Slade

[57] ABSTRACT

A bone nail for the treatment of upper arm fractures comprises a hollow shank adapted to be introduced into the medullary canal and slotted at the distal end, and an expansion screw adapted to be advanced into the shank through rotation of the screw so as to radially expand the slotted end of the shank. An inner thread is formed on the inner wall of the shank outside the slotted region for cooperation with the expansion screw. At least in the slotted region, the cross sectional profile of the shank is provided with alternating elevations and depressions on the inner surface of the wall of the hollow shank.

17 Claims, 3 Drawing Sheets

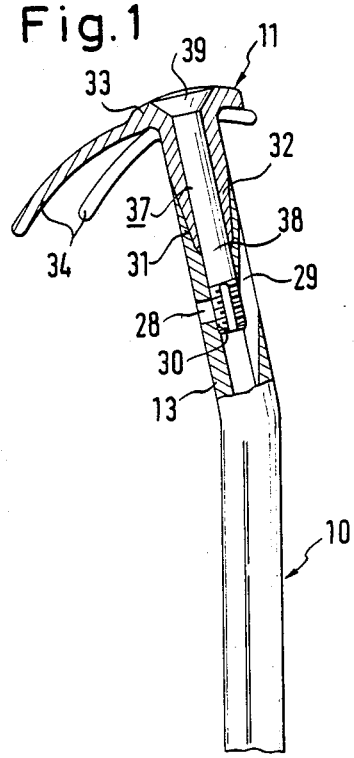
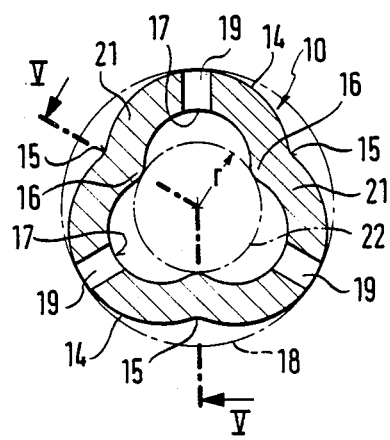
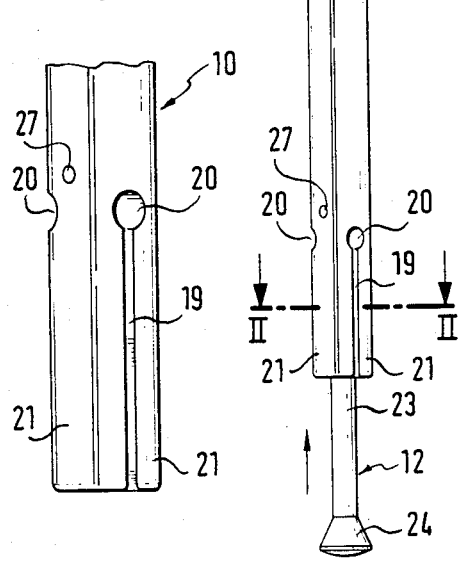
Fig. 1  Fig. 2  Fig. 3  Fig. 4

BONE NAIL FOR THE TREATMENT OF UPPER ARM FRACTURES

BACKGROUND OF THE INVENTION

The invention relates to a bone nail for the treatment of upper arm fractures, comprising a hollow shaft adapted to be introduced proximally into the medullary canal and which is slotted at the distal end, a spreading member cooperating with a screw in the interior of the shank and being pulled into the shank by rotation of the screw and spreading the slotted end.

Nails adapted to be introduced into the medullary canal for the treatment of fractures of hollow cylindrical bones are utilized in many different embodiments with almost all hollow cylindrical bones. So-called interlocking nails have proven to be particularly useful which, with the aid of transverse screws, statically fix the segments of the fracture. Shortening of the bone due to loading during the first phase of healing is thereby avoided. In addition, a high degree of torsional stability is obtained with the aid of an interlocking nail. After removal of the bone screws a dynamic load of the fracture is also possible which is known to stimulate the growth process in the environment of the fracture.

In principle, a locking nail also lends itself well to the treatment of upper arm fractures. Owing to the bone screws, however, the danger exists of important nerves being hurt, so that interlocking nails may be used in upper arm fractures only if the site of fracture is situated in a favourable region.

It is therefore the object of the invention to provide a intramedullary bone nail which is especially suited for the treatment of upper arm fractures.

This object is attained in accordance with the invention in that the profile of the shaft in cross section, at least in the slotted region thereof, has alternating elevations and deepenings at least at the inside thereof, an inner thread being formed in the internal elevations outside the slotted region, and the spreading member being formed by the head of an expansion screw, the shank of which cooperates with the inner thread.

The most favourable site for the introduction of an upper arm bone nail is in the proximal region. Anchoring of the bone nail according to the invention takes place in the distal region by means of dowels. To design a bone nail as an expansion dowel at one end thereof is, on principle, known (European patent 0023228). With the known bone nail, the inside diameter at the distal end is steadily reduced in a direction towards proximal through a corresponding thickening of the wall of the hollow shank of the nail. Cooperating with this inner cone is a conical spreading member which is provided with an inner thread having a screw engaging therein. The head of the screw comes to lie against a guide in the interior of the nail shank. The tool for actuating the screw is introduced from the other end of the shank. Thereby, the spreading member may be pulled into the nail shank and, in doing so, spreads the slotted region of the shank radially outwardly, in order to bring it into engagement with the bone wall.

The known nail shows some disadvantages. To arrange a guide in the interior of the nail and form a thickening in the distal region is very expensive from a manufacturing viewpoint. The maximum diameter of the spreading member must not exceed the outer diameter of the nail, because otherwise the introduction of the bone nail will cause problems. Therefore, the maximum available change in diameter is bound to be limited. The path of adjustment of the spreading member to obtain the maximum spreading is relatively short. Therefore, the maximum spreading which may be obtained at all is relatively small. If, with the known nail, the narrow cross sectional area is exceeded by the spreading member, the fastening in the bone canal will be released again. Therefore, an axial limitation must be provided for the spreading member. When loosening the dowel connection, the screw is rotated in the opposite direction. However, a jamming may occur between the nail wall and the spreading member. It may therefore happen that the screw is completely removed by rotation without the spreading member having moved. In such a case, a blow must be exerted therefore on the head of the screw, in order to release the dowel effect. In this connection, care must be taken that the screw remains connected to the spreading member, otherwise the spreading member will remain in the medullary canal when the nail is being removed.

SUMMARY OF THE INVENTION

With the bone nail according to the invention, the spreading member is formed by the head of a screw which is screwed into an inner thread of the nail shank. This inner thread is cut into inwardly projecting projections of the nail shank. For this purpose, the cross sectional area of the nail has an inner diameter which changes over the circumference thereof, so that deepenings and elevations are formed. What is particularly advantageous is the formation of a so-called cloverleaf profile as has become known per se by the so-called Küntscher type nails. The nail according to the invention preferably has such a profile over the better portion of the length thereof without, however, having a longitudinal slot as is the case with the Küntscher nail. A bone nail with such a cross sectional profile secures the fragments of the fracture more effectively against rotation than is the case with nails having a circular cross section.

In the region of the dowel the above mentioned cross sectional profile of the bone nail according to the invention offers the advantage that the elevations are the same time points of engagement for the spreading head of the spreading screw. According to one embodiment of the invention, the minimum radius defined by the elevations inside the shank of the nail is greater towards the distal end than further inwards. In this manner it is possible to effect a spreading through the spreading head of the screw over the entire length of the spreading region which is determined by the length of the paraxial slots. It goes without saying that the end of the shank of the spreading screw must be provided with means for engagement by a tool to rotate the screw. This means of engagement, according to one embodiment of the invention, may be formed by an inside polygon, such as an inner square, for example.

As already mentioned, owing to the special cross sectional profile of the bone screw according to the invention, not only is the safety against rotation increased for the fracture segments, but there is obtained at the same time a maximum degree of spreading which is determined by the extent of the elevations in the interior of the nail shank. The maximum outside diameter of a nail shank having a cloverleaf profile is, on the contrary, maintained. The loosening of the spreading screw from the nail shank causes no problems, because the screw is supported at the inner thread. So that the screw, however, is not removed inadvertently through rotation, provision is made in one embodiment of the invention for the spreading screw to have an enlargement of diameter at the shank end thereof, with two holes formed in the shank transversely to the longitudinal axis thereof for the accommodation of a security pin and arranged in such a manner that the security pin gets into engagement with the enlargement of diameter when the screw is moved out of the shank by rotation. The position of the security pin and the length of the screw, respectively, are selected to be such that a complete loosening of the head of the screw out of the nail shank must be guaranteed, before the enlargement of diameter gets into engagement with the security pin. The surgeon will perceive from the abutment of the enlargement of diameter against the security pin that this point has been reached.

Another embodiment of the invention provides that two holes oriented transversely to the longitudinal axis of the shank are formed at a small space from the proximal end of the shank for the accommodation of a bone screw. With the aid of a bone screw the nail according to the invention may function as an interlocking nail at one end while the other end is fixed in the manner of an expansion dowel. In this manner a static support of the bone may take place and a shortening during the first healing phase be prevented from occuring. The length of the nail according to the invention may, besides, be adapted to the position of the fracture. The bone nail only needs to be so long that the site of the fracture is sufficiently bridged. In case of fractures disposed near the upper arm joint, therefore, only a relatively short bone nail is required.

Another embodiment of the invention provides that the proximal region of the shank is bent off at a small angle and the wall of the shank is provided with an elongated hole in that region in which the axis of the straight shank portion penetrates through the wall of the bent-off portion.

With a portion bent off the tool for rotating the expansion screw can no longer be passed through the cavity of the nail shank. The bending off, however, it advantageous for anatomical reasons, so that the proximal end of the nail may be placed favourably with a view to the anatomical formation of the upper arm joint. The bent-off portion is correspondingly provided with an elongated hole through which the tool may be introduced. An additional hole must therefore be bored in the head portion of the upper arm, so that the long and thin shank of the tool may be introduced into the bone nail via the elongated hole. But this does not constitute an additional problem for either the operator or the patient.

Another embodiment of the invention provides that two diametrically opposed recesses are formed in the proximal end of the shank. By engagement of a tool in the two recesses the nail may be rotated during and after introduction, in order to respectively impart thereto the most favourable position of rotation and carry out a rotation of the distal fracture segment to align the fracture segments in the anatomically most favourable position of rotation.

According to another embodiment of the invention the proximal shank end may have an inner thread. The inner thread serves to fit a tool for beating in and out.

It may furthermore serve for fitting a target gauge when the bone nail according to the invention is employed as an interlocking nail. In this connection another embodiment of the invention provides that an inner cone is formed on the proximal side of the inner thread which enlarges in a direction towards proximal. The instruments for beating in and out may be provided with corresponding outer cones. The target gauge may likewise be provided with an outer cone, in order to adjust the axial position of the aiming device.

Fractures of the upper arm also will occur directly in the head of the joint. To achieve here, too, an effective treatment, one embodiment of the invention provides that a clamp is connected to the proximal end of the shank said clamp having flexible arms arranged like spiders and slightly bent off downwards. Aligned fracture segments may be intercepted and supported by the associated arms. By correspondingly bending and cutting the arms to length an individual adaptation may be effected to the respective case. Arms not needed may be removed by the operator with the aid of a tong or the like. It goes without saying that such an osteosynthesis aid may also be used with an expansion dowel designed in a conventional manner.

The arms are if possible arranged to be equally spaced circumferentially. However, arms are not required to be available over the entire circumference. It will suffice if a region of about 200° is covered by individual arms. In order to optimize the adaptation of the clamp and the arms, respectively, to the respective fracture, it is possible in accordance with another embodiment of the invention to select the rotational position of the clamp. An adjustment of the rotational position ad libitum is obtained in accordance with another embodiment of the invention in that the clamp is provided in the center thereof with an axial conical journal which cooperates with an inner cone of the shank, said journal having an axial throughbore for a fastening screw the head of which comes to lie in close contact against the outside of the clamp and the shank of which cooperates with the bearing shank. The head of the fastening screw preferably is countersunk into the clamp and provided with an outer rounding the radius of which is approximately in register with the radius of the outer surface of the arms.

DETAILED DESCRIPTION OF THE INVENTION

The invention will be described in the following in more detail by way of drawings.

FIG. 1 shows partly in section an upper arm bone nail according to the invention.

FIG. 2 shows a sectional view of the nail according to FIG. 1 taken along line 2—2.

FIG. 3 shows on an enlarged scale the distal region of the nail according to FIG. 1.

FIG. 4 shows a lateral view partly in section of the proximal nailing region of the nail according to FIG. 1.

Figure 5:
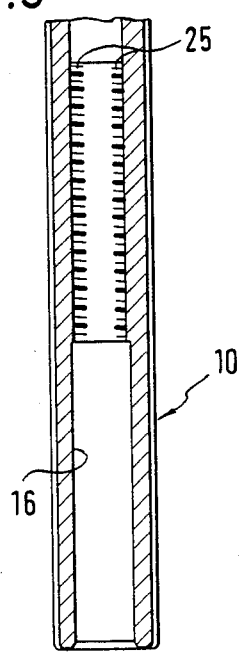
FIG. 5 shows a sectional view of the representation according to FIG. 2 taken along line 5—5.

Prior to enlarging in more detail on the individual representations shown in the drawings it has to be stated that each of the features described is of inventively essential significance by itself or in connection with features of the claims.

The upper arm bone nail shown in FIG. 1 comprises a shank 10, with a clamp 11 fitted at the proximal end thereof while cooperating with an expansion screw 12 at the distal end thereof. The shank 10 has a section 13 in the upper quarter thereof which is bent off at a small angle vis-á-vis the axis of the remaining section. The cross sectional area of the section 13 is circularly shaped, that is inside and outside. The cross sectional area of the remaining shank 10 may be recognized from FIG. 2. The cross sectional profile is in the shape of a three-leafed cloverleaf with three arcuate elevations 14 which are equally spaced circumferentially through 120°, with the arc of an elevation 14 extending through about 180°. Formed between the elevations are deepenings 15 or grooves. The elevations 14 merge with the deepenings 15 through rounded regions. The wall thickness of the shank is uniform over the circumference so that there results a corresponding profile inside with inner elevations 16 and inner deepenings 17. Manufacture of the bone nail as shown takes place starting out from a blank of circular-shaped cross section which is brought into the cross sectional profile as shown in FIG. 2 by cold forming. The outer diameter of the blank is indicated by the circle 18 shown in dash-dotted lines. It will be noted that in the region of the elevations 14 the outside diameter of the blank is maintained.

Formed in the distal end region of the shank 10 are three paraxial slots 19. As will be seen from FIG. 2, they are disposed in the region of the maximum of the elevations 14. They terminate in apertures 20 the diameter of which is greater than the width of the slots 19. In this manner, three laminations 21 are provided the connection of which to the shank has imparted thereto a narrow cross sectional area through the apertures 20. A sort of resilient joint is thus formed in the region of the apertures 20. Formed on the side of the apertures 20 facing away from the distal end is a threaded section in the interior of the shank 10. The threaded section is formed exclusively in the elevations 16 the radius of which is indicated by the dash-dotted circle 22. This radius r, besides, changes in the region of the slots 19 in such a manner that it is greatest at the distal end and smallest immediately in front of the apertures 20. This is obtained, for example, by correspondingly boring open the tubular blank conically.

Figure 7:
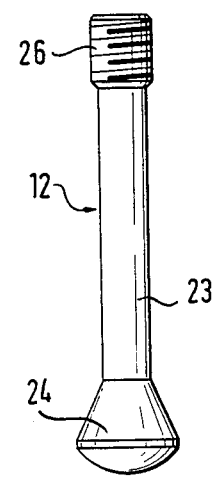
FIG. 7 shows a side view of the expansion screw of the bone nail according to FIG. 1.

The threaded section as mentioned serves for the accommodation of the shank 22 of the expansion screw 12. In FIG. 5 the thread is designated with 25. In FIG. 7 the expansion screw 12 is shown on an enlarged scale. Only the shank end has a threaded portion 26 which has a greater diameter than the remaining shank 23. Formed in the nail shank 10 are two transversely aligned apertures one of them being shown at 27. A safety pin inserted into the apertures 27 prevents the screw 12 being threaded too far out of the bearing shank 10.

Figure 6:
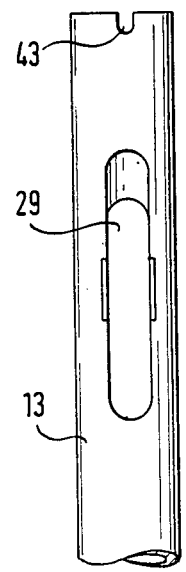
FIG. 6 shows a side view of the proximal end region of the nail according to FIG. 4.

Formed in the angled-off portion 12 of the shank 10 is a transverse bore 28. Disposed diametrically opposite the transverse bore is an elongated hole 29 (see also FIG. 6). The elongated hole is formed in prolongation of the longitudinal axis of the lower portion of the shank 10 in the wall of the angled-off portion 13. The thin, long shank of a tool is introduced into the shank 10 through the elongated hole 29, in order to rotate the expansion screw 12. For this purpose, the expansion screw has a square or hexagonal member at the end of its shank 23, which is not shown in the Figures. A bone screw may be threaded transversely through the bore 28 and the slot 29, in order to axially fix the shank 10 in the corresponding fracture segment.

Figure 8:
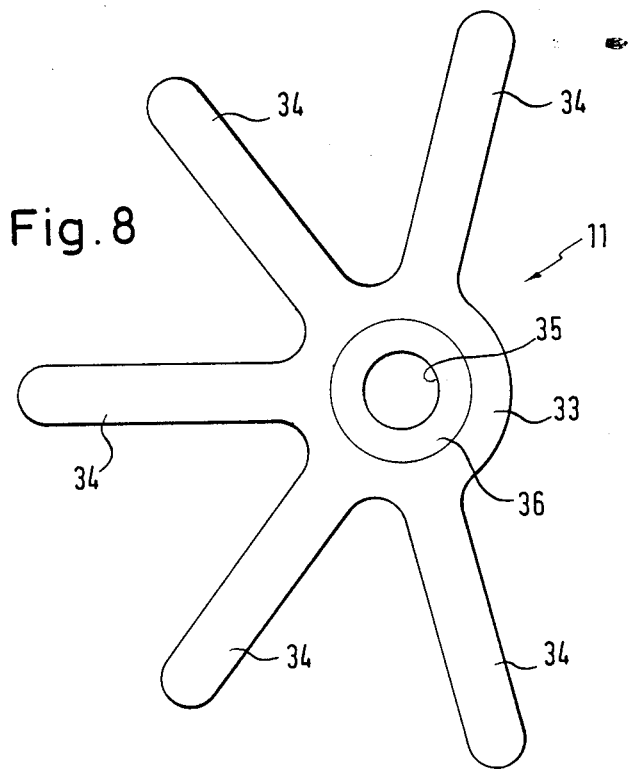
FIG. 8 shows a top plan view taken on a clamp for the bone nail according to FIG. 1.
Figure 9:
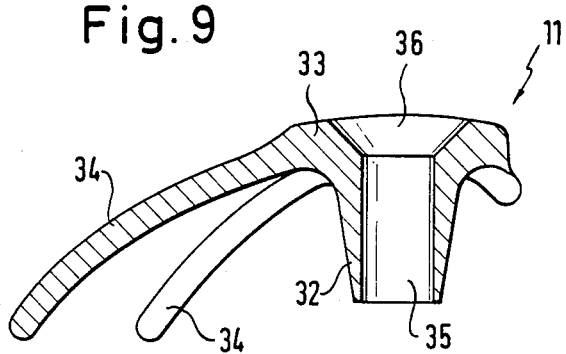
FIG. 9 shows a sectional view taken of the bearing member according to FIG. 8.

The section 13 is provided with an inner thread 30 which extends as far as an inner cone 31 (see FIG. 1) at the proximal end of the shank 10. Cooperating with the inner cone 31 the diameter of which increases in a direction towards proximal is a conical journal 32 of the clamp 11. The inner cone 31, however, may also cooperate with a corresponding outer cone of a tool for beating in and out as well as with a target gauge for fitting a bone screw, whereupon it will still be enlarged in more detail later on. The clamp 11 may be recognized in more detail from FIGS. 8 and 9. In the embodiment according to FIG. 1 the nail must be beaten in to be countersunk which offers the advantage that after a certain progress in the healing process and so-called dynamization during which the clamp and an optional transverse screw are removed, no metal will restrict the mobility of the joint any longer.

Figure 10:
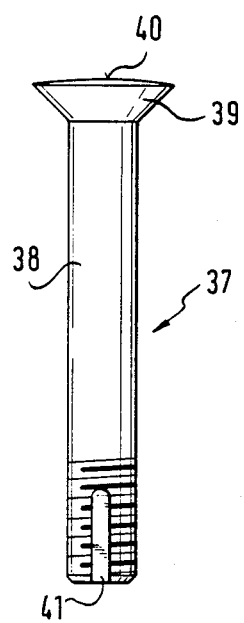
FIG. 10 shows a side view of the fastening screw for the clamp according to FIGS. 8 and 9.

Formed integrally at the inner end of the journal 32 is a radial annular flange 33 having five equally spaced arms 34 integrally formed thereat. The arms describe a region of approximately 200°, while in the remaining region there are no arms present. The spider-shaped arms 34 are circularly bent downwards as may be recognized in FIG. 9, and surround the journal 32 and 32', respectively, like a basket. They are sufficiently flexible, in order to be bent upwards or downwards as required. They may in addition be shortened or completely cut off with the aid of a tong or the like. The flange 33 is rounded at the upper surface (see FIG. 9), with the radius of this rounding approximately being in register with the radius of the arms 34. The journal 32 is provided with a throughbore 35, which enlarges conically upwards at 36. Passed through the throughbore 35 is a fastening screw 37 which is shown on an enlarged scale in FIG. 10. The threaded shank 38 of the fastening screw 37 is threaded into the inner thread 30 (FIG. 4) of the shank 10. The head 39 of the screw 37 is conical and is accommodated by the inner cone 36 of the clamp 11. The outer surface of the screw is rounded as at 40, with said rounding being in conformity with the rounding at the upper surface of the annular flange 33 (see also FIG. 1). Fitted at the end of the shank 38 is a known-per-se safety element 41 of synthetic material, in order to avoid inadvertent loosening of the fastening screw 37.

The mode of operation of the bone nail as described is as follows. After an introduction hole has been bored in the upper arm bone in the proximal end region thereof or has been formed therein in some other manner, the shank 10 with the expansion screw 24 accommodated therein is driven into the medullary canal without the clamp 11. The diameter of the head 24 of the expansion screw 12 is not greater than the outer diameter of the shank 10. The tool for beating in may have a cone cooperating with the inner cone 31 at the proximal end region of the shank 10. As will be seen from FIG. 6, the proximal end comprises two diametrically opposed slot-like recesses 43. The correspondingly designed tool for beating in engages within the recesses 43, so that the shank 10 may be rotated about its axis. This is carried out for the purpose of pruning the fracture segments. When the shank 10 has been completely beaten in, another hole is bored for a tool to actuate the expansion screw 12. This tool comprises a thin long shank which is introduced into the shank 10 through the elongated hole 29 and cooperates with the inner polygonal member of the shank 23 of the expansion screw 12. The screw 12 is threaded into the shank 10, with its head 24 through engagement at the elevations 16 radially spreading the laminations 21 outwardly into engagement with the bone wall, until a tight fit is obtained in the bone.

The shank 10 may be axially fixed in the upper region of the upper arm bone with the aid of a bone screw passed through the bores 28 and 29. A shortening of the bone is thereby avoided and the rotational stability increased. The aiming device for the detection of the bores 28, 29 may likewise comprise a cone cooperating with the inner cone 31 of the shank 10 as well as with the slot-like recesses 43. The bone screw and clamp may be removed after a certain period of time when a sufficient formation of callus has taken place at the fracture site. Thereafter the nail is effective as a dynamic osteosynthesis aid in that it allows alternate loading of the bone. This is known to promote the growth of bone. At this time or also before that already the clamp 11 may be fitted. The position of rotation corresponds to the fractures in the region of the joint head. The arms 34 are correspondingly bent, removed and/or shortened. The clamp 11 is tightly connected to the shank with the aid of the fastening screw 37. If the clamp 11 is inserted with the first treatment, a certain compression will also take place between the dowel and the clamp, which is likewise desired in many cases of treatment. The screw 27 is self-locking, so that it will not loosen by itself.

If the bone nail is to be removed, the clamp 11 if it has been applied and not removed before, will be removed at first. Subsequently, the expansion screw 12 is threaded out of the shank 10 with the aid of the tool already mentioned. The safety pin stucking in the bores 27 is seized by the threaded portion 26 of the screw 12, so that the operator may know when the expansion member 24 has been sufficiently far removed out of the shank 10. Besides, the safety pin prevents the expansion screw 12 being completely turned out thus remaining in the medullary canal when the nail is removed.

As already mentioned, the shank 10 is formed by a straight tubular blank. Since an inner thread has to be formed in the angled-off portion 13, the shank is bored open to a greater diameter in the remaining portion. During this manufacturing step, also the cutting of the inner thread 30 takes place as well as the shaping of the inner cone 31. Thereafter, the straight portion of the shank 10 is brought into a profile according to FIG. 2 by cold forming. Subsequently, the slots 19 are formed and the inner thread is cut into the inner elevations 16. Owing to the manner of production as described the bone nail is approximately free of burrs and therefore has a high degree of stability.

We claim:

1. A bone nail for the treatment of upper arm fractures comprising an elongated hollow shank adapted to be introduced proximally into the medullary canal, the shank having proximal and distal ends and being slotted at the distal end with a plurality of paraxial slots, the transverse cross sectional profile of the shank being provided at least in the slotted region with alternating elevations and depressions on the inner surface of the wall of the hollow shank, and with an inner thread being formed on the inner wall of the hollow shank outside and adjacent to the slotted region; and an expansion screw comprising a head and a shank capable of cooperating with said inner thread, with said expansion screw being adapted to be advanced into the distal end of the shank by rotation of the screw so that the screw head radially expands the slotted distal shank end.

2. A bone nail of claim 1 wherein said paraxial slots are located at the maxima of said elevations.

3. A bone nail of claim 2 wherein each of said slots terminates at its proximal end in a bore the diameter of which is greater than the width of the slot.

4. A bone nail of claim 1 wherein said cross sectional profile in the slotted region has approximately the shape of a three-leafed cloverleaf.

5. A bone nail according to claim 2 wherein the inner radius defined by the alternating elevations on said inner surface of said wall of said hollow shank in said slotted region progressively decreases in the proximal direction.

6. A bone nail of claim 1 wherein the expansion screw includes an enlarged diameter threaded portion at its shank end, with a pair of apertures aligned transversely to the longitudinal shank axis being formed in the shank for the accommodation of a safety pin and arranged in such a manner that the safety pin inserted into said apertures contacts said enlarged diameter portion to prevent removal of the screw from the shank through rotation.

7. A bone nail of claim 1 wherein a polygonal recess is provided in the free end of the screw shank for the accommodation of the matching polygonal end of a screw turning tool.

8. A bone nail of claim 1 wherein two apertures are provided adjacent the proximal end of the nail shank for the accommodation of a bone screw aligned transversely to the axis of the shank.

9. A bone nail for the treatment of upper arm fractures comprising an elongated hollow shank adapted to be introduced proximally into the medullary canal, the shank having proximal and distal ends and being slotted at the distal end with a plurality of paraxial slots, the transverse cross sectional profile of the shank being provided at least in the slotted region with alternating elevations and depressions on the inner surface of the wall of the hollow shank, and with an inner thread being formed on the inner wall of the hollow shank outside the slotted region; and an expansion screw comprising a head and a shank capable of cooperating with said inner thread, with said expansion screw being adapted to be advanced into the shank by rotation of the screw so that the screw head radially expands the slotted distal shank end, wherein a portion of the nail shank in the proximal region of the shank is bent off at a small angle with respect to the remainder of the shank, and an elongated hole aligned with an extension of the longitudinal axis of said remainder of the shank is provided in the wall of said bent off shank portion.

10. A bone nail of claim 1 wherein two diametrically opposed slot-like recesses are formed at the proximal end of the nail shank.

11. A bone nail of claim 1 wherein an inner thread is formed on the inner wall of the hollow shank in said bent off shank portion, with said inner thread being spaced from the proximal extremity of the shank.

12. A bone nail of claim 11 wherein the inner wall of the hollow shank terminates at its proximal end in an inner cone which enlarges in the proximal direction, said inner cone being formed on the proximal side of said inner thread.

13. A bone nail for the treatment of upper arm fractures comprising an elongated hollow shank adapted to be introduced proximally into the medullary canal the shank having proximal and distal ends; an expansion member, with the shank and expansion member being adapted to function together as an expansion dowel at the distal shank end; and a clamp adapted to be connected to the proximal end of the elongated shank and said clamp comprising a body and a plurality of slightly distally bent flexible arms arranged like spider legs.

14. A bone nail according to claim 13 wherein said flexible arms number at least three and are arranged only in a circumferential region of about 200° around said clamp body, said flexible arms being equally spaced circumferentially within said about 200° circumferential region.

15. A bone nail of claim 13 wherein the angular position of the clamp about the axis of the elongated shank is adjustable.

16. A bone nail of claim 15 wherein the clamp includes a conical journal in the body thereof which is adapted to cooperate with an inner cone formed in the proximal end of the nail shank, said journal having an axial throughbore for receiving a fastening screw the shank of which is adapted to cooperate with an inner thread formed on the inner wall of the hollow shank and the head of which is intended to lie against the outer surface of the clamp when the clamp is fastended to the shank.

17. A bone nail of claim 16 wherein the head of the fastening screw and the outer surface of the clamp body are both rounded in a complementary manner so that they form together a uniform smoothly rounded surface when the clamp is fastened by means of the fastening screw to the shank.

* * * * *